United States Patent [19]

Berger et al.

[11] Patent Number: 4,732,902

[45] Date of Patent: Mar. 22, 1988

[54] PYRROLOISOQUINOLINYL-DIMETHYLOXOALKYL ALKONOATES AND THEIR USE AS ANTIPSYCHOTIC AGENTS

[75] Inventors: Leo Berger, Montclair; Gary L. Olson, Westfield, both of N.J.

[73] Assignee: Hoffmann-La Roche Inc., Nutley, N.J.

[21] Appl. No.: 866,532

[22] Filed: May 23, 1986

[51] Int. Cl.$^4$ .................. A61K 31/40; A61K 31/435; C07D 471/04; C07C 67/02
[52] U.S. Cl. ........................... 514/292; 514/284; 546/84; 546/70; 560/262; 560/185
[58] Field of Search .................. 546/84, 70; 560/262, 560/185; 514/292, 284

[56] References Cited

U.S. PATENT DOCUMENTS 4,260,762 4/1981 Berger et al. ..................... 546/84
4,334,070 6/1982 Berger et al. ..................... 546/70

OTHER PUBLICATIONS

C.A. 28-Heterocycles, vol. 84 1976 84: 121690T.
CA 35 Synthetic High Polymers, vol. 79, 1973 67040n.
C.A. 23-Aliphatics, vol. 78, 1973 71478h.
C.A. vol. 77, 1972 74835n.
C.A. 23-Aliphatics, vol. 76, 1972-3405r.
C.A. vol. 69, 1968 51496y.
C.A. vol. 75, 1971-5191w.
C.A. 28-Heterocycles, vol. 96, 1982 96:199688j.
C.A. vol. 100, 1984-100:34529c.
C.A. vol. 93, 1980 93: 185705V.

*Primary Examiner*—Henry R. Jiles
*Assistant Examiner*—J. Richter
*Attorney, Agent, or Firm*—Jon S. Saxe; Bernard S. Leon; William G. Isgro

[57] ABSTRACT

The invention relates to long-acting depot producing antipsychotic pyrroloisoquinolinyl-dimethyloxoalkyl alkanoates of the formula

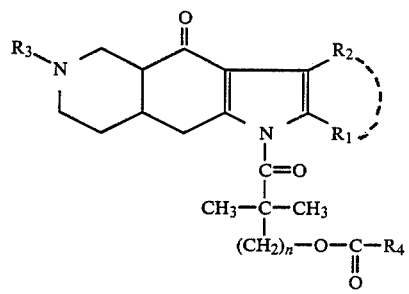

wherein $R_1$ and $R_2$ independently, are hydrogen, alkyl of 1 to 4 carbon atoms, cycloalkyl or alkenyl, or taken together are alkylene of 3 to 6 carbon atoms; and $R_3$ is hydrogen, alkyl, hydroxyalkyl, phenylhydroxyalkyl, halophenylhydroxyalkyl, alkylphenylhydroxyalkyl, alkoxyphenylhydroxyalkyl, alkoxyalkyl, aryloxyhydroxyalkyl, alkoxyhydroxyalkyl, acyloxyalkyl, arylcarbonylalkyl, alkoxycarbonylalkyl, aralkyl, alkenyl, alkylcycloalkyl, alkynyl, thienylalkyl, furylalkyl, arylcarboxamidoalkyl, acylalkyl, cyclic-alkyloxoalkyl, cyclic-alkylhydroxyalkyl, alkenyloxyalkyl, aralkenyl, aryloxyalkyl, or aryl-N-imidazolonylalkyl; $R_4$ is alkyl; and n is the integer 2 or 3, their corresponding optical isomers, geometric isomers, and mixtures thereof, and the pharmaceutically acceptable acid additional salts.

The compounds of formula I are useful as antipsychotic agents.

33 Claims, No Drawings

PYRROLOISOQUINOLINYL-DIMETHYLOXOALKYL ALKONOATES AND THEIR USE AS ANTIPSYCHOTIC AGENTS

BRIEF SUMMARY OF THE INVENTION

The invention relates to long-acting depot prodrug antipsychotic pyrroloisoquinolinyl-dimethyloxoalkyl alkanoates of the formula

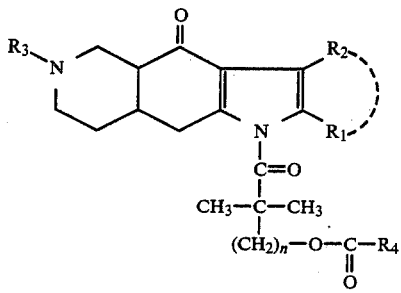

wherein $R_1$ and $R_2$ independently, are hydrogen, alkyl of 1 to 4 carbon atoms, cycloalkyl or alkenyl, or taken together are alkylene of 3 to 6 carbon atoms, preferably 3 to 4 carbon atoms; and $R_3$ is hydrogen, alkyl, hydroxyalkyl, phenylhydroxyalkyl, halophenylhydroxyalkyl, alkylphenylhydroxyalkyl, alkoxyphenylhydroxyalkyl, alkoxyalkyl, aryloxyhydroxyalkyl, alkoxyhydroxyalkyl, acyloxyalkyl, arylcarbonylalkyl, alkoxycarbonylalkyl, aralkyl, alkenyl, alkylcycloalkyl, alkynyl, thienylalkyl, furylalkyl, arylcarboxamidoalkyl, acylalkyl, cyclic-alkyloxoalkyl, cyclic-alkylhydroxyalkyl, alkenyloxyalkyl, aralkenyl, aryloxyalkyl, or aryl-N-imidazolonylalkyl; $R_4$ is alkyl; and n is the integer 2 or 3 and their pharmaceutically acceptable acid addition salts.

DETAILED DESCRIPTION OF THE INVENTION

As used herein, the term "alkyl", when undefined, preferably denotes a straight or branched chain saturated hydrocarbon containing 1 to 24 carbon atoms, for example, methyl, ethyl, propyl, isopropyl, butyl, t-butyl, pentyl, heptyl, octyl, decyl, dodecyl and the like, preferably, alkyl is 7 to 11 carbon atoms. It is noted that the term "alkoxy" preferably denotes "lower alkoxy", which denotes an alkyl ether group in which the lower alkyl group is as described above, for example, methoxy, ethoxy, propoxy, pentoxy, and the like. The term "alkenyl" preferably denotes "lower alkenyl", which denotes a straight or branched chain unsaturated hydrocarbon containing 2 to 7 carbon atoms, for example, vinyl, allyl, and the like. The term "alkynyl" preferably denotes "lower alkynyl", which denotes a straight or branched chain unsaturated hydrocarbon containing 2 to 7 carbon atoms, for example, ethynyl, propargyl, methylbutynyl, and the like. The term "halogen" or "halo" denotes all the halogens, i.e. bromine, chlorine, fluorine, and iodine. The term "aryl" denotes phenyl or phenyl bearing one or more substituents selected from the group consisting of halogen, trifluoromethyl, lower alkyl, lower alkoxy, nitro, amino, lower alkylamino, and di-lower alkylamino. The term "aralkyl" preferably denotes benzyl and the like. The term "aryloxy" denotes an aryl ether group in which the aryl group is as described above, for example, phenoxy and the like. The term "acyl" denotes an "alkanoyl" group derived from an aliphatic carboxylic acid of 1 to 7 carbon atoms, for example, formyl, acetyl, propionyl, and the like; and an "aroyl" group derived from an aromatic carboxylic acid, such as benzoyl and the like. The term "acyloxy" denotes an "alkanoyloxy" group derived from an aliphatic carboxylic acid of 1 to 7 carbon atoms, for example, formyloxy, acetoxy, propionyloxy, and the like; and an "aroyloxy" group derived from an aromatic carboxylic acid, such as benzoyloxy and the like. The term "cyclic-alkyl" denotes a cycloalkyl group of 3 to 6 carbon atoms, that is, cyclopropyl, cyclobutyl, cyclopentyl and cyclohexyl, or a bicycloalkyl group such as bornyl or a tricycloalkyl group such as adamantyl. The term arylcarbonylalkyl denotes an aryloxoalkyl group, for example, 3-phenyl-3-oxopropyl, 4-(4-fluorophenyl)-4-oxobutyl, and the like.

The invention relates to pyrroloisoquinolinyl-dimethyloxoalkyl alkanoates of the formula

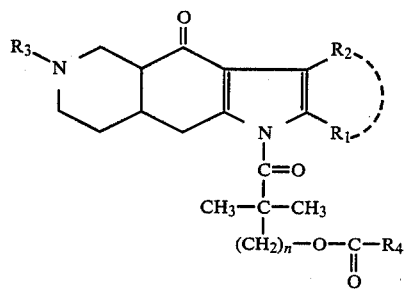

wherein $R_1$ and $R_2$ independently, are hydrogen, alkyl of 1 to 4 carbon atoms, cycloalkyl or alkenyl, or taken together are alkylene of 3 to 6 carbon atoms; and $R_3$ is hydrogen, alkyl, hydroxyalkyl, phenylhydroxyalkyl, halophenylhydroxyalkyl, alkylphenylhydroxyalkyl, alkoxyphenylhydroxyalkyl, alkoxyalkyl, aryloxyhydroxyalkyl, alkoxyhydroxyalkyl, acyloxyalkyl, arylcarbonylalkyl, alkoxycarbonylalkyl, aralkyl, alkenyl, alkylcycloalkyl, alkynyl, thienylalkyl, furylalkyl, arylcarboxamidoalkyl, acylalkyl, cyclic-alkyloxoalkyl, cyclic-alkylhydroxyalkyl, alkenyloxyalkyl, aralkenyl, aryloxyalkyl, or aryl-N-imidazolonylalkyl; $R_4$ is alkyl; and n is the integer 2 or 3 their corresponding optical isomers, geometric isomers, and mixtures thereof and their pharmaceutically acceptable acid addition salts, which can be prepared as hereinafter described.

The geometric isomers, hereinbefore referred to, are characterized by the formulas

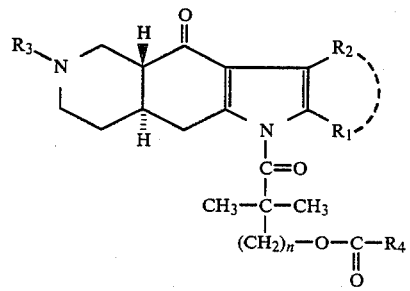

trans-I

-continued

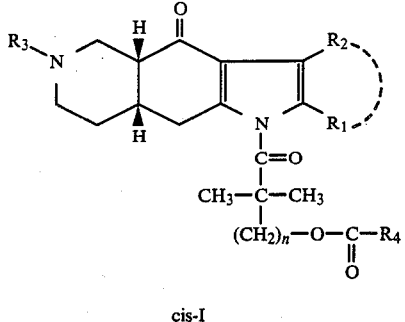

cis-I wherein $R_1$, $R_2$, $R_3$, and $R_4$ and n are as hereinbefore described.

A preferred group of compounds comprises the trans compounds of formula trans-I wherein $R_1$ and $R_2$ are alkyl of 1 to 4 carbon atoms or together are alkylene of 3 to 4 carbon atoms, $R_3$ is alkyl, arylcarbonylalkyl or aralkyl, n is 2, and $R_4$ is alkyl.

A more preferred group of compounds comprises the trans compounds of formula trans-I wherein $R_1$ and $R_2$ are alkyl of 1 to 4 carbon atoms, $R_3$ is alkyl, and $R_4$ is alkyl of 7–11 carbons.

A still more preferred group of compounds comprises the trans compounds of formula trans-I, which are the 4aR, 8aR enantiomers, wherein $R_1$ and $R_2$ are alkyl of 1 to 4 carbon atoms, $R_3$ is alkyl, and $R_4$ is alkyl of 7–11 carbons.

A most preferred compound is: 2,6-Dimethyl-1-[2,2-dimethyl-4-[(1-oxodecyl)oxy]-1-oxo-butyl]-3-ethyl-1,4a,5,6,7,8,8a,9-octahydro-4a,8a-trans-4H-pyrrolo[2,3-g]isoquinolin-4-one;

Exemplary of the compounds of formula I are:

2,6-Dimethyl-2-[2,2-dimethyl-4-[(1-oxohexyl)oxy]-1-oxo-butyl]-3-ethyl-1,4a,5,6,7,8,8a,9-octahydro-4a,8a-trans-4H-pyrrolo[2,3-g]isoquinolin-4-one;

2,6-Dimethyl-1-[2,2-dimethyl-4-[(1-oxoheptyl)oxy]-1-oxobutyl]-3-ethyl-1,4a,5,6,7,8,8a,9-octahydro-4a,8a-trans-4H-pyrrolo[2,3-g]isoquinolin-4-one;

2,6-Dimethyl-1-[2,2-dimethyl-4-[(1-oxohexadecyl)oxy]-1-oxobutyl]-3-ethyl-1,4a,5,6,7,8,8a,9-octahydro-4a,8a-trans-4H-pyrrolo[2,3-g]isoquinolin-4-one;

2,6-Dimethyl-1-[2,2-dimethyl-4-[(1-oxooctyl)oxy]-1-oxobutyl]-3-ethyl-1,4a,5,6,7,8,8a,9-octahydro-4a,8a-trans-4H-pyrrolo[2,3-g]isoquinolin-4-one;

2,6-Dimethyl-1-[2,2-dimethyl-4-[(1-oxododecyl)oxy]-1-oxobutyl]-3-ethyl-1,4a,5,6,7,8,8a,9-octahydro-4a,8a-trans-4H-pyrrolo[2,3-g]isoquinolin-4-one;

2,6-Dimethyl-1-[2,2-dimethyl-4-[(1-oxooctadecyl)oxy]-1-oxobutyl]-3-ethyl-1,4a,5,6,7,8,8a,9-octahydro-4a,8a-trans-4H-pyrrolo[2,3-g]isoquinolin-4-one;

2,6-Dimethyl-1-[2,2-dimethyl-4-[(1-oxoeicosanoyl)oxy]-1-oxobutyl]-3-ethyl-1,4a,5,6,7,8,8a,9-octahydro-4a,8a-trans-4H-pyrrolo[2,3-g]isoquinolin-4-one;

2,6-Dimethyl-1-[2,2-dimethyl-4-[(1-oxooctyl)oxy]-1-oxobutyl]-3-ethyl-1,4a,5,6,7,8,8a,9-octahydro-4a,8a-trans-4H-pyrrolo[2,3-g]isoquinolin-4-one, maleate;

(−)-2,6-Dimethyl-1-[2,2-dimethyl-4-[(1-oxodecyl)oxy]-1-oxo-butyl]-3-ethyl-1,4a,5,6,7,8,8a,9-octahydro-4aR,8aR-4H-pyrrolo[2,3-g]isoquinolin-4-one;

2-Methyl-6-(1-phenylmethyl)-1-[2,2-dimethyl-4-[(1-oxodecyl)oxy]-1-oxobutyl]-3-ethyl-1,4a,5,6,7,8,8a,9-octahydro-4H-4a,8a-trans-pyrrolo[2,3-g]isoquinolin-4-one;

2-Methyl-6-(2-phenylethyl)-1-[2,2-dimethyl-4-[(1-oxodecyl)oxy]-1-oxobutyl]-3-ethyl-1,4a,5,6,7,8,8a,9-octahydro-4H-4a,8a-trans-pyrrolo[2,3-g]isoquinolin-4-one;

2,3-Dimethyl-6-{[1-[4-(4-fluorophenyl)-4-oxobutyl]}-1-{2,2-dimethyl-4-[(1-oxodecyl)oxy]-1-oxobutyl}-1,4a,5,6,7,8,8a,9-octahydro-4a,8a-trans-4H-pyrrolo[2,3-g]isoquinolin-4-one;

(−)-2,3-Dimethyl-6-{[1-[4-(4-fluorophenyl)-4-oxobutyl]}-1-{2,2-dimethyl-4-[(1-oxodecyl)oxy]-1-oxobutyl}-1,4a,5,6,7,8,8a,9-octahydro-4aR,8aR-4H-pyrrolo[2,3-g]isoquinolin-4-one;

2-Methyl-6-(2-hydroxy-2-phenylethyl)-1-[2,2-dimethyl-4-[(1-oxodecyl)oxy]-1-oxobutyl]-3-ethyl-1,4a,5,6,7,8,8a,9-octahydro-4H-4a,8a-trans-pyrrolo[2,3-g]isoquinolin-4-one;

trans-1,3,4,4a,5,6,7,8,9,10a-decahydro-6-[2,2-dimethyl-1-oxo-4-[(1-oxodecyl)oxy]butyl]-2-methylcyclopenta[4,5]pyrrolo[2,3-g]isoquinolin-10(2H)-one;

trans-1,3,4,4a,5,6,7,8,9,10a-decahydro-6-[2,2-dimethyl-1-oxo-4-[(1-oxohexyl)oxy]butyl]-2-methylcyclopenta[4,5]pyrrolo[2,3-g]isoquinolin-10(2H)-one;

trans-1,3,4,4a,5,6,7,8,9,10a-decahydro-6-[2,2-dimethyl-1-oxo-4-[(1-oxooctyl)oxy]butyl]-2-methylcyclopenta[4,5]pyrrolo[2,3-g]isoquinolin-10(2H)-one;

trans-1,3,4,4a,5,6,7,8,9,10a-decahydro-6-[2,2-dimethyl-1-oxo-4-[(1-oxododecyl)oxy]butyl]-2-methylcyclopenta[4,5]pyrrolo[2,3-g]isoquinolin-10(2H)-one;

trans-1,3,4,4a,5,6,7,8,9,10a-decahydro-6-[2,2-dimethyl-1-oxo-4-[(1-oxododecyl)oxy]butyl]-2-[4-(4-fluorophenyl)-4-oxobutyl]cyclopenta[4,5]pyrrolo[2,3-g]isoquinolin-10(2H)-one trans-1,3,4,4a,5,6,7,8,9,10-decahydro-6-[2,2-dimethyl-1-oxo-4-[(1-oxodecyl)oxy]butyl]-2-methylcyclohexa[4,5]pyrrolo[2,3-g]isoquinolin-11(2H)-one, which is also named as: trans-1,2,3,4,4a,5,6,7,8,9,10,11a-dodecahydro-6-[2,2-dimethyl-1-oxo-4-[(1-oxodecyl)oxy]butyl]-2-methyl-11H-pyrido[4,3-b]carbazol-11-one;

and the like.

The compounds of formula I can be prepared as set forth in Reaction Scheme I.

REACTION SCHEME I

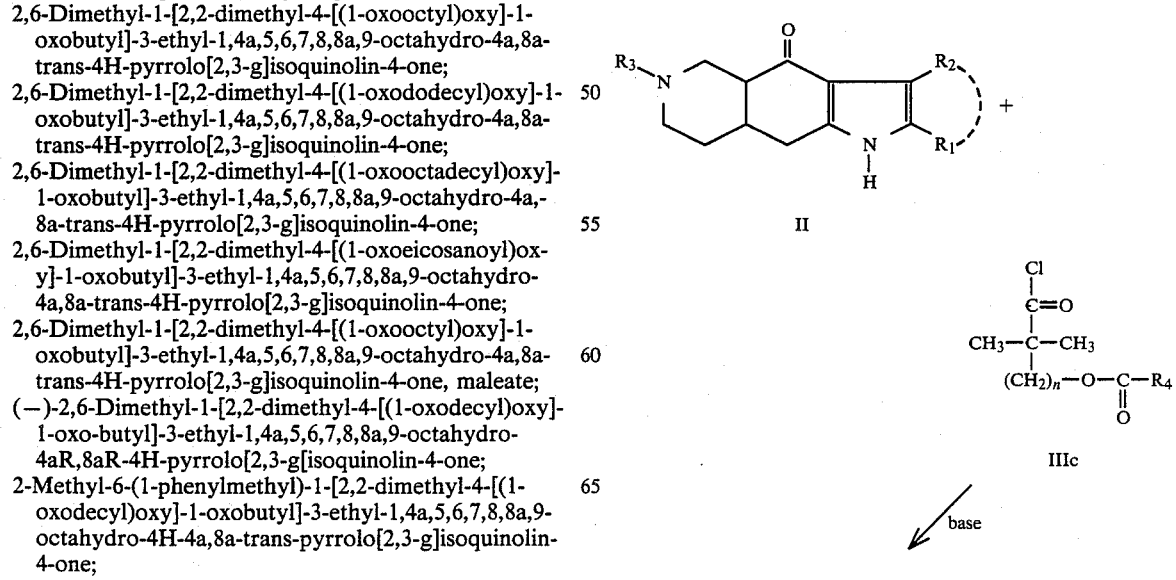

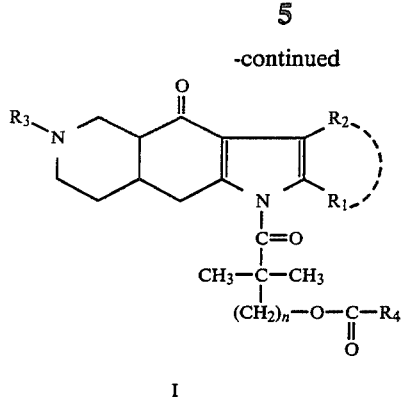

I

In accordance with Scheme I, compounds of formula I may be prepared by acylation of known pyrroloisoquinoline derivatives of formula II with an acyl halide of formula IIIc. The reaction may be carried out in the presence of a base, for example by formation of the anion of compound II with n-butyllithium in tetrahydrofuran, dimsyl sodium in dimethyl sulfoxide, or a lithium dialkylamide, such as lithium diisopropylamide in tetrahydrofuran. Temperatures below 0° C. are preferred, especially −30° C. to −50° C., to reduce the amount of isomerization leading to a 4a,8a-cis isomer of the product. After formation of the anion, the acyl halide of formula IIIc is added to produce the acylated product compound I. In cases where there are functional groups present in substituents $R_1$, $R_2$ and $R_3$ in the compound of formula II which could react under the acylating conditions, these groups may be protected by reaction with suitable protecting groups. After the acylation, such groups may be removed to yield the desired compounds I. For example, when a compound of formula I wherein $R_3$ contains a hydroxyl group is desired, the hydroxyl group in II may be protected with a group such as a t-butyldimethylsilyl group, a benzyl group, or a 2-ethoxyethyl or 2-tetrahydro-pyranyl group using established methods of protection and deprotection (see, T. W. Greene, Protective Groups in Organic Synthesis, Wiley, 1981, Ch.2). Similarly, when the compound of formula II has an enolizable carbonyl group in $R_3$, the yield in the condensation may be improved by protecting the carbonyl group by established methods (ibid. ch. 4).

The starting materials of formula IIIc can be prepared as set forth in Reaction Scheme II.

Reaction Scheme II

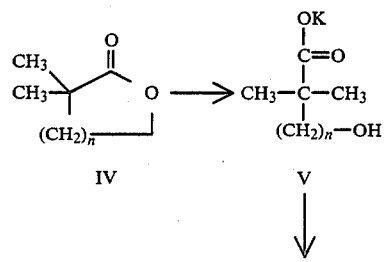

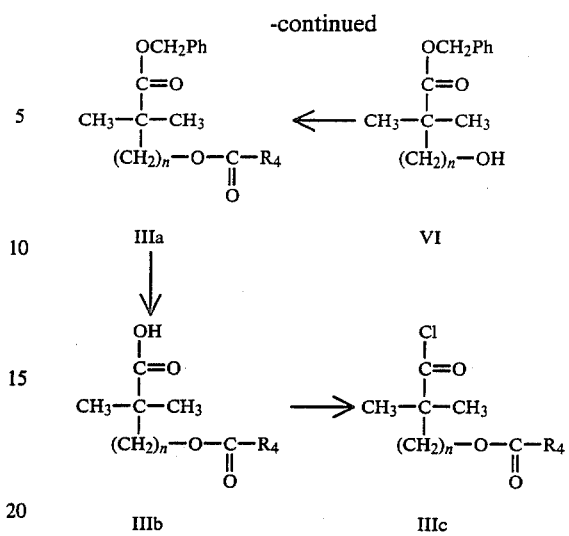

In accordance with Scheme II, the acyl halides of formula IIIc may be prepared by either of the two procedures described in Schemes II and III. In the process described in Scheme II, a 3,3-dimethyl-substituted lactone IV is employed as a starting material. Treatment of the lactone IV with aqueous potassium hydroxide affords the monopotassium salt V. Benzylation of V, for example, with benzyl bromide in dimethylformamide gives the hydroxybenzyl ester VI. Esterification of VI using an alkanoyl halide of from 1 to 24 carbon atoms in the presence of a base such as 4-dimethylaminopyridine in methylene chloride leads to the acylated benzyl ester IIIa. Catalytic hydrogenolysis of IIIa using palladium hydroxide on carbon affords the corresponding carboxylic acid IIIb, which is converted to the acyl halide IIIC by treatment with a halogenating reagent, such as thionyl chloride or oxalyl chloride.

Scheme III

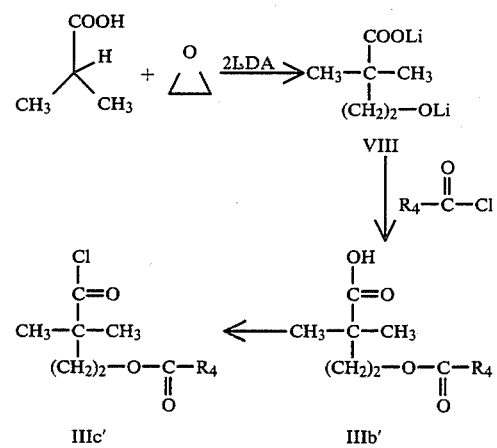

The alternative route described in Scheme III may be employed to prepare compounds of the formula IIIc' which are used to prepare compounds of formula I wherein n is 2. In this method, the dianion of isobutyric acid is prepared by treatment of isobutyric acid with two equivalents of lithium diisopropylamide in tetrahydrofuran, and is then treated with ethylene oxide. The resulting solution containing the dilithium salt is then treated with an alkanoyl halide of from 1 to 24 carbon atoms to yield the acylated carboxylic acid of formula IIIb' in a single step. The conversion of the acid IIIb' to acid chloride IIIc' is carried out identically to that for the conversion of the acid IIIb to the acid chloride IIIc, described in Scheme II.

The compounds of formula I can form acid addition salts with inorganic or organic acids. Thus, they form pharmaceutically acceptable acid addition salts with both pharmaceutically acceptable organic and inorganic acids, for example, with hydrohalic acid, such as, hydrochloric acid, hydrobromic acid, hydroiodic acid, other mineral acid salts, such as, sulfuric acid, nitric acid, phoshoric acid, perchloric acid or the like, alkyl and mono-aryl sulfonic acids such as, ethanesulfonic acid, toluenesulfonic acid, benzenesulfonic acid, or the like, other organic acids such as acetic acid, tartaric acid, maleic acid, citric acid, benzoic acid, salicylic acid, ascorbic acid and the like. Non-pharmaceutically acceptable acid addition salts of compounds of formula I can be converted into pharmaceutically acceptable acid addition salts via conventional metathetic reactions whereby the non-pharmaceutically acceptable anion is replaced by a pharmaceutically acceptable anion; or alternatively, by neutralizing the non-pharmaceutically acceptable acid addition salt and then reacting the so-obtained free base with a reagent yielding a pharmaceutically acceptable acid addition salt.

However, preferably the bases of formula I which are soluble in oil are utilized.

The compounds of formula I, and if desired their pharmaceutically acceptable acid addition salts, exhibit antipsychotic activity. The activity of the compounds of formula I can be demonstrated in warm-blooded animals, in accordance with known procedures, as hereinafter described.

Compounds of formula I are prodrugs which exhibit antipsychotic-like activity in animal models by virtue of their enzymatic cleavage to liberate compounds of formula II, which are known antipsychotic agents. The tests described hereinafter demonstrate that activity of compounds of formula I as prodrugs and establish their antipsychotic activity and duration of action in animals. With the proper choice of chain length in the group $R_4$ in compounds of formula I, the duration of action can be varied to provide, for example, a long-term antipsychotic effect after a single administration. When the compound of formula I has $R_1$=methyl, $R_2$=ethyl, $R_3$=methyl, the action of enzymes releases the compound of formula II wherein $R_1$=methyl, $R_2$=ethyl, $R_3$=methyl which is a known dopamine antagonist and antipsychotic agent in man, also referred to as piquindone.

Spiroperidol binding test. In the absence of esterases which trigger the release of the compound of formula II from the compound of formula I, there is only weak activity in the 3H-spiroperiodol binding assay, an in vitro test which measures binding to dopamine receptors. In this test, rat striatal brain homogenates were incubated for 20 min. in the presence of 0.2 nanomolar $^3$H-spiroperidol and varying concentrations of test compounds. The incubations were terminated by rapid filtration through Whatman GF/B filters. followed by 2×5 mL washes with ice-cold assay buffer (50 mM tribase-HCl pH 7.7 which contains fixed concentrations of 0.1% ascorbic acid, 120 mM sodium chloride, 5 mM potassium chloride, 2 mM calcium chloride, and 1 mM magnesium chloride).

TABLE 1

H—Spiroperidol Binding in vitro of compounds of formula I wherein $R_1$ = $CH_3$, $R_2$ = $CH_2CH_3$, $R_3$ = $CH_3$; $R_4$ = as in table

| compd. | ester ($R_4CO$) | $R_4$ | $IC^{50}$, nM |
|---|---|---|---|
| Ia | acetate | $CH_3$ | 250 |
| Ib | octanoate | $C_7H_{15}$ | 195 |
| Ic | decanoate | $C_9H_{19}$ | 870, 1000 |
| Id | dodecanoate | $C_{11}H_{23}$ | 570 |
| Ie | palmitate | $C_{15}H_{31}$ | 640 |
| If | stearate | $C_{17}H_{35}$ | 1000 |
| Ig | eicosanoate | $C_{19}H_{39}$ | 1000 |

Demonstration of the enzymatic cleavage of compounds of formula I was demonstrated in vitro by incubating compounds of formula I with rat liver homogenate. In this test, acetone solutions of the test compounds (0.5 μmole/50 μL) were added to an incubation medium consisting of 2.7 ml 0.1M potassium hydrogenphosphate (pH 7.4) and 0.3 ml rat liver 9,000×g supernatant. The media were then incubated for 1 hour at 37° C. Controls consisted of a sample containing the complete medium and substrate which was not incubated, a sample containing only phosphate buffer and substrate, and a sample containing the complete medium but lacking substrate.

The incubation media were fractionated with a Waters C-18 SEP-PAK. Prior to sample application, the SEP-PAK was washed with 10 ml of methanol and 20 ml of water. After sample application, the SEP-Pak was washed with 10 ml of water and 3 ml of methanol. The amount of the liberated compound of formula II was measured by high pressure liquid chromatography on a 30-cm Waters μ-Bondapak C-18 column, equilibrated with 70:30:1 methanol:water:ammonium hydroxide. Results are given in Table 2.

TABLE 2

Esterase Cleavage of Prodrug Esters of Formula I

| Compd. | Ester | $R_4$ | Formation of IIa ($R_1$ = $CH_3$, $R_2$ = $CH_2CH_3$, $R_3$ = $CH_3$; piquindone) as % of incubated test compound I in 1 hr. |
|---|---|---|---|
| Ia | acetate | $CH_3$ | 88 ± 2.0 |
| Ib | acetanoate | $C_7H_{15}$ | 104.1 ± 3.3 |
| Ic | decanoate | $C_9H_{19}$ | 102 ± 0.0 |
| Id | dodecanoate | $C_{11}H_{23}$ | 77.2 ± 0.8 |
| Ie | palmitate | $C_{15}H_{31}$ | 31 ± 1.0 |
| If | stearate | $C_{17}H_{35}$ | 12.1 ± 0.4 |
| Ig | eicosanoate | $C_{19}H_{39}$ | 11.7 ± 0.7 |

Because compounds of formula I may have a long aliphatic ester chain, such as $R_4$=$C_7H_{15}$, $C_9H_{19}$, $C_{11}H_{21}$, and the like, they are soluble in non-polar solvents including alkanes such as hexane, cyclohexane, octane and the like. They are also soluble in oils and fats, and in particular may be used in parenteral formulations, for example, intramuscular or subcutaneous as a solution or suspension in oils which are known to form depots upon injection, from which the compound is released over a prolonged period into the blood stream. In the case of compounds of formula I, a preferred mode of administration is intramuscular injection in sesame oil solution. When administered in this fashion, compounds of formula I may exhibit a long duration of action. This extended duration of action is thought to be due to a slow diffusion of the compound of formula I from the oil depot into surrounding tissues or plasma.

After diffusing from the depot, the action of esterases cleaves the acyl group

from the remainder of the molecule which spontaneously hydrolyzes to release the antipsychotic compounds of formula II. The process is illustrated in Scheme IV.

SCHEME IV

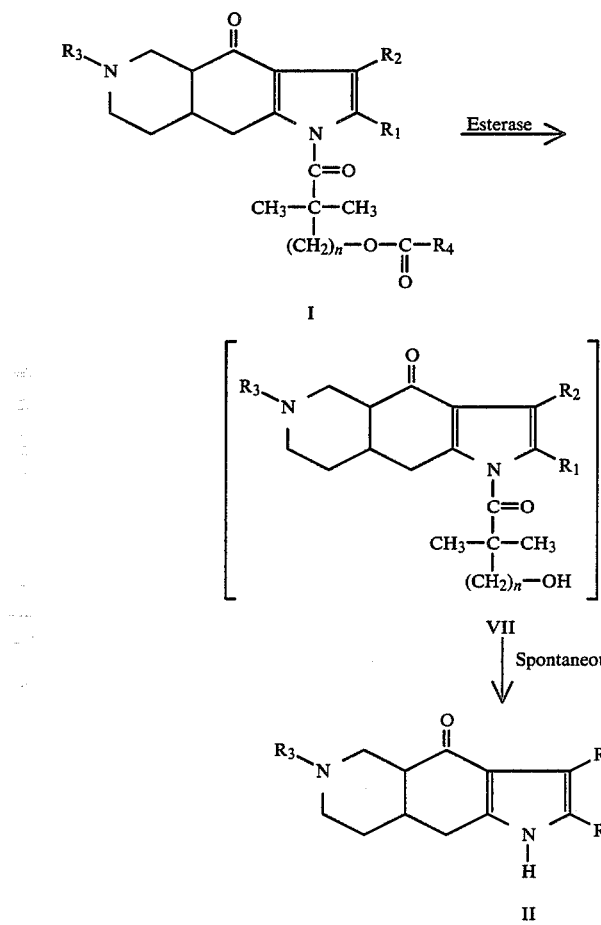

In Reaction Scheme IV, the intermediate hydroxy Compound VII undergoes a spontaneous hydrolysis to liberate the compound of formula II. The duration of action of compounds of formula I thus may be altered by choosing different chain lengths of the group $R_4$, as well as by altering the rate of diffusion of the compound of formula I by changing the nature of the oil depot.

In vivo activity. Pole Climb Avoidance Test. In the pole climb test, antipsychotics characteristically disrupt an acquired discrete conditioned avoidance behavior in doses well below those which suppress the response to unconditioned stimuli (escape). The principle of the test procedure was described by Courvoisier S. et al. (Arch. Int. Pharmacodyn 92, 305, 1954), Cook, L. et al. (Ann. N.Y. Acad. Sci. 66, 740-752, 1957) and Pfeiffer, C. et al. (Ann, N.Y. Acad. Sci. 66, 753-764, 1957).

The animals were male SPF rats (stock Fuellinsdorf Albino, outbred) weighing 200-220 g at the end of a discrete conditioned avoidance training.

The test apparatus was a sound-attenuated plexiglass chamber (41×30×30 cm). The floor was a grid consisting of 27 stainless steel rods, to which a scrambled current of 0,8 mA could be delivered by means of a stimulator. The safety area was a vertical pole (4,3 cm diameter, 24 cm long) attached to the top of the chamber. The free lower end of the pole was 6 cm above the grid floor. A buzzer was mounted within the testing enclosure.

Training

The rats were placed in the plexiglass chamber and trained to jump to the pole during a buzzer stimulus (conditioned stimulus CS) lasting 10 sec, in order to avoid an immediately following electrical footshock (unconditioned stimulus US) of 30 sec duration delivered to the grid floor in addition to the CS. If the rat climbed to the pole during the CS or CS plus US, the stimuli (buzzer, footshock) were immediately terminated.

The pole climb response occurring during the CS period is called an avoidance response or conditioned response (CAR or CR), that occurring during exposure to CS plus US escape response of unconditioned response (UER or UR). Following one training trial (exposure to one CS and US respectively) the rats were returned to their home cage. After 15-17 trials rats were jumping during the buzzer stimulation only and were ready for drug testing.

Drug Experiment

A group of 10 trained rats was used per dose (graded doses, geometric progression: factor 3.16). The test compounds were administered intramuscularly in a sesame oil solution containing 25 mg of compounds per ml of solution.

Dose-effect curves of block of conditioned response (BCR) were constructed by plotting the log dose against the effect (in percent BCR) at the peak of action. From these curves the ED50 for BCR were graphically determined. The potency of a drug for suppressing CR was expressed by the ED50 for BCR. For the evaluation of the long-term effect, a drug dose eliciting a non-supra-maximal 90-100% block of avoidance response within 24 hours was followed up at 24 hour intervals. Results are given in Table 3.

TABLE 3

Effect and Duration of Prodrug Esters I ($R_1 = CH_3$, $R_2 = CH_2CH_3$, $R_2 = CH_3$; $R_4 = $ as in table) in Rat Pole Climb Avoidance Test.

| | | | Blockade of Avoidance Response (BAR) | | | |
|---|---|---|---|---|---|---|
| | | | Acute (mg/kg) | | Duration | |
| Compound | Ester | $R_4$ | $ED_{50}$ | 100% BAR dose | % BAR | Day # |
| Ia | acetate | $CH_3$ | 0.6 | 3.0 | 90 | 1 |
| | | | | | 50 | 2 |
| Ic | decanoate | $C_9H_{19}$ | 3.6 | 10 | 100 | 1 |
| | | | | | 100 | 2 |
| | | | | | 100 | 3 |
| | | | | | 90 | 4 |
| | | | | | 80 | 5 |
| | | | | | 50-60 | 6-13 |
| Ie | palmitate | $C_{15}H_{31}$ | 17 | 30 | 100 | 1 |
| | | | | | 10 | 2 |
| If | stearate | $C_{17}H_{35}$ | 16.2 | 30 | 100 | 1 |
| | | | | | 10 | 2 |
| Ig | eicosanoate | $C_{19}H_{39}$ | 13.8 | 30 | 100 | 1 |

TABLE 3-continued

Effect and Duration of Prodrug Esters I ($R_1$ = $CH_3$, $R_2$ = $CH_2CH_3$, $R_2$ = $CH_3$; $R_4$ = as in table) in Rat Pole Climb Avoidance Test.

| Com- pound | Ester | $R_4$ | Acute (mg/kg) $ED_{50}$ | Blockade of Avoidance Response (BAR) 100% BAR dose | Duration % BAR | Day # |
|---|---|---|---|---|---|---|
| | | | | | 10 | 2 |

A compound of formula I or a salt thereof, or a composition containing a therapeutically effective amount of a compound of formula I or a salt thereof can be administered by methods well known in the art. Thus, a compound of formula I or a salt thereof can be administered either singly or with other pharmaceutical agents, for example, parenterally by intramuscular injection in oil, to achieve a long duration action.

The compounds of formula I, their corresponding optical isomers, geometric isomers and mixtures thereof and their pharmaceutically acceptable acid addition salts can be used in the form of conventional depot parenteral pharmaceutical preparations. By way of exemplification, suitable dosage units comprise or are in the range of from 5 to 500 mg.

For a suitable dosage regimen a compound may be administered at intervals of from 1 day to 8 weeks, with the administered dose being calculated by multiplying the interval between doses in days by amount of compounds to be administered in the range of from about 0.1 mg/kg to about 10 mg/kg.

However, for any particular warm-blooded animal, the specific dosage regimen may be variable and should be adjusted according to individual need, the potency of the administered compound and the professional judgment of the person administering or supervising the administration of a compound of formula I or a pharmaceutically acceptable acid addition salt thereof. Furthermore, the frequency with which any such dosage form will be administered will vary, depending upon the quantity of active medicament present therein and the needs and requirements of the pharmacological situation.

Since the compounds of formula I and their pharmaceutically acceptable acid addition salts possess asymmetric carbon atoms, they are ordinarily obtained as racemic mixtures. The resolution of such racemates into the optically active isomers can be carried out by known procedures. Some racemic mixtures can be precipitated as eutectics and can thereafter be separated. Chemical resolution is, however, preferred. By this method, diastereomers are formed from the racemic mixture with an optically active acid, such as (+)-tartaric acid to form a diastereomeric salt. The formed diastereomers are separated by fractional crystallization and can be converted to the corresponding optical isomer base. Thus, the invention covers the optically active isomers of the compounds of formula I as well as their racemates. Alternatively, one can start with optically active starting materials and obtain the corresponding enantiomeric end products.

Furthermore, due to the possible different spatial arrangements of their atoms, it is to be understood that the compounds of this invention may be obtained in more than one possible geometric isomeric form. The compounds of formula I, as described and claimed, are intended to embrace all such isomeric forms. Accordingly, the examples included herein are to be understood as illustrative of particular mixtures of geometric isomers or single geometric isomers and not as limitations upon the scope of the invention.

The examples which follow further illustrate the invention. All temperatures are in degrees Centigrade unless otherwise stated.

EXAMPLE 1

Preparation of 2,2-Dimethylbutyrolactone

To a solution of diisopropylamine (15.9 g) in tetrahydrofuran (160 mL) was added a solution of n-butyllithium in hexane (150 mL) at $-40°$ to $-60°$ C., and the solution was stirred for 20 minutes. 2-Methylbutyrolactone (0.150 mol) was added and the solution was stirred at $-50°$ C. for 15 minutes. Methyl iodide (23.5 g) was added and the solution was allowed to warm slowly over ca. 1 hour to room temperature. The solution was then cooled in an ice bath and 2N hydrochloric acid (150 ML) was added, and the mixture was transferred to a separatory funnel and extracted with ether. The combined extracts were washed with brine, dried (sodium sulfate) and evaporated. The product was distilled to afford 12.3 g (72%) of 2,2-dimethylbutyrolactone as a colorless oil: bp 65°–66° C./10 mm.

EXAMPLE 2

Preparation of 4-Hydroxy-2,2-dimethylbutanoic acid, monopotassium salt

A mixture of 2,2-dimethylbutyrolactone (6.84 g) and potassium hydroxide (3.36 g) in water (60 mL) was heated to reflux with a drop of phenolphthalein indicator. After 15 minutes the pink color disappeared and the solution was kept at reflux for 2 hours, then concentrated to dryness at 50° C./1 mm. The crude salt, 4-hydroxy-2,2-dimethylbutanoic acid, monopotassium salt was dissolved in ethanol and ether was added to give a white solid precipitate which was filtered off and dried at 100° C./1 mm to afford 8.05 g (80%) of hydroxyacid salt, 4-hydroxy-2,2-dimethylbutanoic acid, monopotassium salt: mp 219°–221° C.; IR (KBr) 3260 (OH) and 1580, 1557 cm$^{-1}$ (COO$^-$); NMR (DMSO) δ 1.00 (s, 6, $CH_3$), 1.52 (t, 2, $CH_2$), and 3.46 (t, 2, $CH_2$).

Anal. Calcd for $C_6H_{11}O_3K$: C, 42.33; H, 6.51. Found: C, 42.51; H, 6.56.

EXAMPLE 3

Preparation of 4-Hydroxy-2,2-dimethylbutanoic acid phenylmethyl ester

A mixture of benzyl bromide (37.4 g) and 4-hydroxy-2,2-dimethylbutanoic acid, monopotassium salt, (3.4 g) in dimethylformamide (35 mL) was stirred at room temperature for 18 hours. The precipitate was filtered off and the filtrate was evaporated. The residue was chromatographed on silica gel eluting with 2:1 dichloromethane:ethyl acetate to give 3.95 g (89%) of 4-hydroxy-2,2-dimethylbutanoic acid phenylmethyl ester as a colorless oil. A sample was evaporatively distilled to give the analytical sample: bp 160°–165° C./0.25 mm; IR (CHCl$_3$) 3595 (OH), 1707 (C=O) and 687 cm$^{-1}$ (C$_6$H$_5$); NMR (CDCl$_3$) δ 1.23 (s, 6, $CH_3$), 1.85 (t, 2, $CH_2$), 3.67 (t, 2, $CH_2$), 5.11 (s, 2, $CH_2$) and 7.34 (s, 5, Ph); MS m/e 222,91.

Anal. Calcd for $C_{13}H_{18}O_3$: C, 70.24, H, 8.16. Found: C, 70.48; H, 8.14.

EXAMPLE 4

The esters listed in Table I were prepared in an analogous manner to that described in this example.

TABLE I

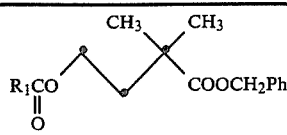

9

| Examples | $R_1$ | bp[1] | Yield | Formula | Analytical Data Calcd. (%) | Found (%) |
|---|---|---|---|---|---|---|
| 5 | $CH_3$ | 160° C./0.02 mm | 60.5% | $C_{15}H_{20}O_4$ | C 68.16<br>H 7.63 | C 68.20<br>H 7.71 |
| 6 | $C_7H_{15}$ | 185–195° C./0.03 mm | 88.0% | $C_{21}H_{32}O_4$ | C 72.38<br>H 9.28 | C 72.13<br>H 9.08 |
| 7 | $C_9H_{19}$ | 190° C./0.15 mm | 74.5% | $C_{23}H_{36}O_4$ | C 73.37<br>H 9.64 | C 73.57<br>H 9.71 |
| 8 | $C_{11}H_{23}$ | 210° C./0.04 mm | 90.0% | $C_{25}H_{40}O_4$ | C 74.22<br>H 9.97 | C 74.09<br>H 9.86 |
| 9 | $C_{15}H_{31}$ | 215–225° C./0.02 mm | 71.0% | $C_{29}H_{48}O_4$ | C 75.61<br>H 10.50 | C 75.71<br>H 10.41 |
| 10 | $C_{17}H_{35}$ | 220° C./0.02 mm | 72.5% | $C_{31}H_{52}O_4$ | C 76.18<br>H 10.72 | C 75.98<br>H 10.98 |
| 11 | $C_{19}H_{39}$ | 225–230° C./0.02 mm | 57.0% | $C_{33}H_{56}O_4$ | C 76.69<br>H 10.92 | C 76.91<br>H 10.67 |

[1]Evaporatively distilled

Preparation of 2,2-Dimethyl-4[(1-oxodecyl)oxy]butanoic acid phenylmethyl ester To a solution of 4-hydroxy-2,2-dimethylbutanoic acid phenylmethyl ester (1.11 g), in dichloromethane in an ice bath, was added dimethylaminopyridine (0.72 g) followed by a solution of decanoyl chloride (0.95 g) in dichloromethane (5 mL). The mixture was stirred at room temperature for 2 hours and was filtered. The filtrate was evaporated and the residue was chromatographed on silica gel eluting with dichloromethane to afford 1.4 g (74.5%) of 2,2-dimethyl-4-[(1-oxodecyl)oxy]butanoic acid phenylmethyl ester. A portion was evaporatively distilled to give an analytical sample as a colorless oil: bp 190° C./0.15 mm; IR (CHCl$_3$) 1720 (C=O) and 697 cm$^{-1}$(Ph); NMR (CDCl$_3$) δ 0.87 (t, 3, CH$_3$), 1.25–1.60 (m, 20, CH$_2$ and CH$_3$), 1.93 (t, 2, CH$_2$), 2.23 (t, 2, CH$_2$), 4.11 (t, 2, CH$_2$), 5.11 (s, 2, CH$_2$) and 7.33 (s, 5, Ph); MS m/e 376 and 91.

Anal. Calcd for C$_{23}$H$_{36}$O$_4$: C, 73.37; H, 9.64 Found: C, 73.57; H, 9.71

EXAMPLE 12

Preparation of 2,2-Dimethyl-4-[(1-oxodecyl)oxy]butanoic acid

A mixture of 2,2-dimethyl-4-[(1-oxodecyl)oxy]butanoic acid phenylmethyl ester (33.9 g), 20% Pd(OH)$_2$/C (2.0 g), and ethanol (150 mL) was hydrogenated at 50 psi at room temperature for 2 hours, filtered to remove the catalyst, and concentrated to afford 24.9 g (96.5%) of 2,2-dimethyl-4-[(1-oxodecyl)oxy]butanoic acid as a colorless oil. A portion was evaporatively distilled to afford an analytical sample: bp 190° C./0.02 mm; IR (CHC$_3$) 1733 (C=O) and 1704 cm$^{-1}$ (C=O); NMR (CDCl$_3$) δ 0.87 (t, 3, CH$_3$), 1.60–1.24 (m, 20, CH$_2$ and CH$_3$), 1.93 (t, 2, CH$_2$), 2.25 (t, 2, CH$_2$), 4.14 (t, 2, CH$_2$); MS m/e 268 (M$^+$ —H$_2$O).

Anal. Calcd for C$_{16}$H$_{30}$O$_4$: C, 67.10; H, 10.56 Found: C, 67.01; H, 10.72.

The esters listed in Table II were prepared in an analogous manner to that described in this example.

TABLE II

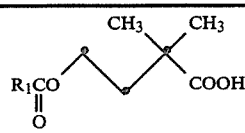

| Examples | $R_1$ | bp[1] | mp | Yield[2] | Formula | Calcd (%) | Found (%) | Cryst. From |
|---|---|---|---|---|---|---|---|---|
| 13 | $CH_3$ | 150–160° C./0.02 | — | — | $C_8H_{14}O_4$ | C 55.16<br>H 8.10 | C 55.01<br>H 8.08 | — |
| 14 | $C_7H_{15}$ | 180–190° C./0.1 mm | — | — | $C_{14}H_{26}O_4$ | C 65.09<br>H 10.14 | C 64.71<br>H 10.29 | — |
| 15 | $C_9H_{19}$ | 190° C./0.02 | — | — | $C_{16}H_{30}O_4$ | C 67.10<br>H 10.56 | C 67.01<br>H 10.72 | — |
| 16 | $C_{11}H_{23}$ | — | 30–34° C. | — | $C_{18}H_{34}O_4$ | C 68.75<br>H 10.90 | C 68.72<br>H 10.81 | hexane |
| 17 | $C_{15}H_{31}$ | — | 49–50° C. | — | $C_{22}H_{42}O_4$ | C 71.31<br>H 11.42 | C 71.16<br>H 11.45 | hexane |

TABLE II-continued

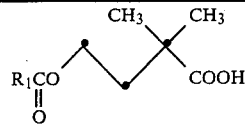

| Examples | R₁ | bp[1] | mp | Yield[2] | Formula | Calcd (%) | Found (%) | Cryst. From |
|---|---|---|---|---|---|---|---|---|
| 18 | $C_{17}H_{35}$ | — | 55–56° C. | — | $C_{24}H_{46}O_4$ | C 72.31<br>H 11.63 | C 71.88<br>H 11.32 | hexane |
| 19 | $C_{19}H_{39}$ | — | 62–63° C. | — | $C_{26}H_{50}O_4$ | C 73.19<br>H 11.81 | C 72.69<br>H 11.69 | hexane |

Evaporatively distilled
Crude product used in subsequent step.

EXAMPLE 20

Preparation of 2,2-dimethyl-4-[(1-oxodecyl)oxy]butanoic acid from isobutyric acid ("one-pot process")

To a suspension of sodium hydride (0.16 g) in dry tetrahydrofuran (5 mL) was added dropwise with stirring in an ice bath a solution of isobutyric acid (0.352 g) in dry tetrahydrofuran (5 mMol). After the addition, the mixture was warmed to 50°–55° C. for 15 minutes until all hydrogen evolution had stopped, and was then cooled to −30° C. To the solution was added a solution of lithium diisopropylamide (prepared from diisopropylamine (0.40 g) and n-butyllithium (1.1M solution in hexane) in dry tetrahydrofuran (5 mL) at −20° to −30° C.). After the addition, the solution was warmed to 30°–35° C. for 30 minutes and ethylene oxide (2.0 mL, condensed as a liquid in a dropping funnel fitted with a Dry Ice condenser) was added at 0° C. The mixture was then stirred for 1 hour at room temperature. To the solution was added decanoyl chloride (0.76 g) in 10 mL of dry tetrahydrofuran and the solution was stirred at room temperature for 1 hour and then poured onto ice water. The crude product was extracted with dichloromethane, and the combined extracts were washed with brine, dried ($Na_2SO_4$), and evaporated. Chromatography on silica gel (60 g) eluting with 5% MeOH in dichloromethane afforded 0.25 g of 2,2-dimethyl-4-[(1-oxodecyl)oxy]butanoic acid (22.5%). In a larger scale experiment, the crude product was distilled to give the pure decanoate, bp 195°/0.06 mm.

EXAMPLE 21

Decanoic Acid 3-carboxy-3,3-dimethylpropyl ester

A 5-L flask equipped with a mechanical stirrer, thermometer, dropping funnel, and a condenser topped with an nitrogen bubbler was swept with nitrogen and then charged with 44.0 g (1.10 moles contained) of 60% sodium hydride in mineral oil. This material was washed with 3×200 mL=600 mL of bp 35°–60° petroleum ether with the washes being removed by suction pipette. To the damp grey solid was added 3.0L of tetrahydrofuran (freshly filtered through neutral alumina I) and 140.2 mL (101.2 g=1.0 mole) of diisopropylamine (distilled under nitrogen from calcium hydride, bp 81°–83°). This mixture was stirred as 92.7 mL of isobutyric acid was added over 35 minutes. Gas ($H_2$) evolution, the formation of a white precipitate, and a temperature rise to 42° were observed. The suspension was brought to reflux on a steam cone and held at that temperature for 15 minutes as hydrogen evolution came to a virtual halt. The suspension was then cooled in an ice bath to 5° and 400 mL of 2.5M n-butyllithium in hexanes was added over 40 minutes. The temperature remained at 7°–9° during this time as most of the solid disappeared and a cloudy green-gray solution was formed. This mixture was heated to 35°, kept at that temperature for 15 minutes, and cooled again to 5°. To the mixture was added, over 15 minutes, 250 mL (220 g) of ethylene oxide (distilled from the cylinder into an ice-water jacketed dropping funnel). The reaction was exothermic; after 5 minutes and about 100 mL had been added, the temperature had reached 20° and the green-gray color was gone. As the subsequent addition took place, the temperature dropped to 17°. The somewhat gel-like mixture was brought to 4° over 45 minutes and the 207.5 mL (190.7 g) of decanoyl chloride was added over 1.0 hours. The gel broke up and a new precipitate gradually formed as the temperature remained below 8°. The ice bath was kept in place but allowed to melt as stirring was continued for an additional 15 hours. The suspension was poured into a stirred mixture of 4 L of ice-water and 4 L of brine. The pH of the mixture was brought from 13 (paper) to 1 by the addition of 250 mL of concentrated hydrochloric acid. The cloudy solution was extracted with 2 L and 3×1 L=5 L of ether. The combined extracts were washed with 2×500 mL=1.0 L of brine and concentrated on a rotary evaporator at 40°/70 mm to a volume of about 2 L. This solution was dried over sodium sulfate and again stripped to give 316 g of light orange oil. This material was evaporatively (bulb-to-bulb) distilled, changing the receiver as appropriate.

| Cut | Oil Bath Temp/Pressure | Wt. | Appearance |
|---|---|---|---|
| 1 | to 160°/0.02 mm | 9.8 g | orangish-yellow oil |
| 2 | 160°/0.02 mm to 192°/0.05 mm | 44.2 g | light yellow oil |
| 3 | 195°/0.06 m | 184.3 g | very light yellow oil |
| Pot | | 41.5 g | brown oil |

Cut 3 (184.3 g = 64% yield) had an nmr in agreement with the desired structure and a purity, as assessed by gc, of 99%.

EXAMPLE 22

Preparation of 2,2-dimethyl-4-[(1-oxodecyl)oxy]butanoyl chloride

A mixture of the 2,2-dimethyl-4-[(1-oxodecyl)oxy]butanoic acid (24.9 g) and thionyl chloride (24.9 g) was stirred at room temperature for 18 hours and concentrated to dryness to give 24.9 g (94%) of the crude decanoate acid chloride 2,2-dimethyl-4-[(1-oxodecyl)oxy]butanoyl chloride. A portion was evaporatively distilled to afford an analytical sample as a colorless oil: bp 170°–180° C/0.02 mm; IR ($CHCl_3$) 1777(COCl) and 1734 cm$^{-1}$ (C=O); NMR ($CDCl_3$) δ0.88 (t, 3, $CH_3$), 1.28–1.59 (m, 17, $CH_2$), 1.35 (s, 6, $CH_3$), 2.06 (t, 2, $CH_2$), 2.29 (t, 2, $CH_2$), 4.17 (t, 2, $CH_2$); MS m/e 269 (M+—Cl).

Anal. Calcd for $C_{16}H_{29}ClO_3$: C, 63.04; H, 9.59. Found: C, 63.23; H, 9.60.

The esters listed in Table III were prepared in an analogous manner to that described in this example.

TABLE III

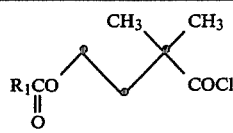

| Examples | $R_1$ | bp[1] | mp | Yield[2] | Formula | Calcd.(%) | Found(%) | Cryst. From |
|---|---|---|---|---|---|---|---|---|
| 23 | $CH_3$ | 105–115° C./0.02 | — | | $C_8H_{13}ClO_3$ | C 49.88 | C 50.12 | — |
| | | | | | | H 6.80 | H 6.72 | |
| 24 | $C_7H_{15}$ | 170–180° C./0.1 mm | — | | $C_{14}H_{25}ClO_3$ | C 60.75 | C 62.72 | — |
| | | | | | | H 9.10 | H 9.85 | |
| 25 | $C_9H_{19}$ | 170–180° C./0.02 mm | — | | $C_{16}H_{29}ClO_3$ | C 63.04 | C 63.23 | — |
| | | | | | | H 9.59 | H 9.60 | |
| 26 | $C_{11}H_{23}$ | 180–190° C./0.0.03 mm | — | | $C_{18}H_{33}ClO_3$ | C 64.94 | C 64.93 | — |
| | | | | | | H 9.99 | H 10.16 | |
| 27 | $C_{15}H_{31}$ | 195–205° C./0.02 mm | — | | $C_{22}H_{41}ClO_3$ | C 67.93 | C 69.64 | |
| | | | | | | H 10.62 | H 10.84 | |
| 28 | $C_{17}H_{35}$ | — | 30–34° C. | | $C_{24}H_{45}ClO_3$ | C 59.12 | C 69.16 | hexane |
| | | | | | | H 10.88 | H 10.72 | |
| 29 | $C_{19}H_{39}$ | — | 41–42° C. | | $C_{26}H_{49}ClO_3$ | C 70.16 | C 70.35 | |
| | | | | | | H 11.10 | H 10.95 | |

[1] Evaporatively distilled
[2] Crude product used in subsequent step

EXAMPLE 30

Preparation of rac.-2,6-dimethyl-1-[2,2-dimethyl-4-[(1-oxodecyl)oxy]-1-oxobutyl]-3-ethyl-1,4a,5,6,7,8,8a,9-octahydro-4a,8a-trans-4H-pyrrolo[2,3-g]isoquinolin-4-one To a solution of diisopropylamine (1.51 g) in tetrahydrofuran (60 mL) was added n-butyllithium in hexane (10.0 mL) at −30° C. and the solution was stirred at −20° to −30° C. for 15 minutes. To the solution was added at −40° to −50° C. (in one portion) rac,-3-ethyl-2,6-dimethyl-1,4a,5,6,7,8,8a,9-octahydro-4a,8a-trans-4H-pyrrolo[2,3 g]isoquinolin-4-one (3.6 g) and the mixture was stirred at −20° to −30° C. for 30 minutes. The mixture becomes a (sometimes slightly cloudy) solution as the anion of rac,-3-ethyl-2,6-dimethyl-1,4a,5,6,7,8-,8a,9-octahydro-4a,8a-trans-4H-pyrrolo[2,3 g]isoquinolin-4-one is formed. To the solution was added the crude 2,2-dimethyl-4-[(1-oxodecyl)oxy]butanoyl chloride (4.5 g) in tetrahydrofuran (15 mL) at −40° to −50° C. over about 1 minute, and the mixture was stirred for an additional 30 minutes. The solution was then poured onto ice water and was extracted with dichloromethane. The combined extracts were washed with brine, dried sodium sulfate and evaporated.

The crude product rac.-2,6-dimethyl-1-[2,2-dimethyl-4-[(1-oxo-decyl)oxy]-1-oxobutyl]-3-ethyl-1,4a,5,6,7,8-,8a,9-octahydro-4a,8a-trans-4H-pyrrolo[2,3-g]isoquinolin-4-one containing a small amount of the corresponding 4a,8a-cis isomer was chromatographed on silica gel eluting with the lower phase of a mixture prepared by shaking 90 parts chloroform, 30 parts methanol, 10 part water, and 6 parts acetic acid to give 4.5 g (58.5%) of the decanoate prodrug rac.-2,6-dimethyl-1-[2,2-dimethyl-4-[(1-oxo-decyl)oxy]-1-oxobutyl]-3-ethyl-1,4a,5,6,7,8,8a,9-octahydro-4a,8a-trans-4H-pyrrolo-[2,3-g]isoquinolin-4-one upon evaporation and neutralization of the chromatographic fractions. The crude product was crystallized from hexane at −20° C. to afford 2.5 g (32.5%) of pure decanoate prodrug rac.-2,6-dimethyl-1-[2,2-dimethyl-4-[(1-oxo-decyl)oxy]-1-oxobutyl]-3-ethyl-1,4a,5,6,7,8,8a,9-octahydro-4a,8a-trans-4H-pyrrolo-[2,3-g]isoquinolin-4-one as an off-white crystalline solid, mp 43°–45° C.: IR (KBr) 1723 (C=O) and 1655 cm$^{-1}$ (C=O); NMR (CDCl$_3$) δ 0.87 (t, 3,, CH$_3$), 1.08 (t, 3, CH$_3$), 1.25–3.0 (m, 26, CH$_2$), 1.31 (s, 6, CH$_3$), 2.10 (s, 3, CH$_3$), 2.34 (s, 3, CH$_3$), 2.63 (t, 2, CH$_2$), 3.49 (br. d, 1, CH), 4.21 (t, 2, CH$_2$); MS m/e 514 (M+).

Anal. Calcd for $C_{31}H_{50}N_2O_4$: C, 72.30; H, 9.79; N, 5.44. Found: C, 71.98; H, 9.81; N, 5.40

In a like manner, if the 4aR, 8aR or 4aS, 8aS-enantiomer of the pyrroloisoquinoline is used, the corresponding enantiomers of the decanoate prodrug can be obtained.

The esters listed in Table IV were prepared in an analogous manner to that described in this example.

TABLE IV

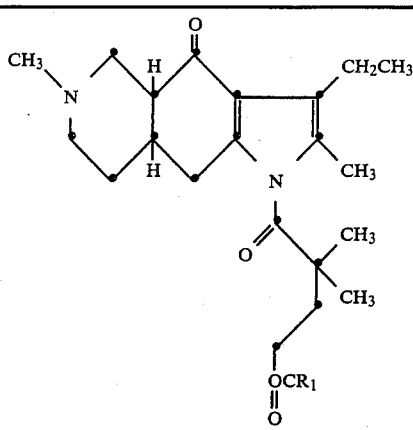

| Examples | R₁ | mp | Yield¹ | Formula | Calcd(%) | Found(%) | Cryst. From |
|---|---|---|---|---|---|---|---|
| 31 | CH₃ | 67–70° C. | 35.5% | C₂₃H₃₄N₂O₄ | C 68.63<br>H 8.51<br>N 6.96 | C 68.67<br>H 8.39<br>N 6.99 | hexane-Et₂O |
| 32 | C₇H₁₅ | 74–77° C. | 22.0% | C₃₃H₅₀N₂O₈ | C 65.76<br>H 8.36<br>N 4.65 | C 65.60<br>H 8.48<br>N 4.68 | EtOAc—Et₂O |
| 33 | C₉H₁₉ | 43–45° C. | 32.5% | C₃₁H₅₀N₂O₄ | C 72.30<br>H 9.79<br>N 5.44 | C 71.98<br>H 9.81<br>N 5.40 | hexane |
| 34 | C₁₁H₂₃ | 48–49° C. | 25.2% | C₃₃H₅₄N₂O₄ | C 73.02<br>H 10.03<br>N 5.16 | C 72.72<br>H 9.73<br>N 5.04 | hexane |
| 35 | C₁₅H₃₁ | 51–53° C. | 22.5% | C₃₇H₆₂N₂O₄ | C 74.20<br>H 10.43<br>N 4.68 | C 74.11<br>H 10.26<br>N 4.46 | hexane |
| 36 | C₁₇H₃₅ | 60–61° C. | 39.6% | C₃₉H₆₆N₂O₄ | C 74.71<br>H 10.61<br>N 4.47 | C 74.40<br>H 10.58<br>N 4.43 | hexane |
| 37 | C₁₉H₃₉ | 65–67° C. | 34.0% | C₄₁H₇₀N₂O₄ | C 75.18<br>H 10.77<br>N 4.28 | C 74.80<br>H 10.96<br>N 4.25 | hexane |

EXAMPLE 38 trans-1,3,4,4a,5,6,7,8,9,10a-Decahydro-6-[2,2-dimethyl-1-oxo-4-[(1-oxodecyl)oxy]butyl]-2-methylcyclopenta[4,5]pyrrolo[2,3-g]isoquinolin-10(2H)-one To a solution of diisopropylamine (0.15 g) in tetrahydrofuran (15 mL) was added n-butyllithium in hexane (0.75 mL, 2M solution) at −20° to −30° and the solution was stirred at −20° to −30° C. for 30 minutes. To the solution was added at −20° to −30° C. (in one portion) trans-1,3,4,4a,5,7,8,9,10,10a-decahydro-2-methyl-6H-cyclopenta[4,5]pyrrolo[2,3-g]isoquinolin-10(2H)-one (0.244 g) and the mixture was stirred at −20° C. for 2 hours. To the solution was added the crude 2,2-dimethyl-4-[(1-oxodecyl)oxy]butanoyl chloride (0.45 g) in tetrahydrofuran at −20° to −30° and the mixture was stirred at this temperature for an additional 1 hour. The mixture was poured onto ice water and extracted in the dichloromethane. The combined dichloromethane extracts were washed with brine dried sodium sulfate and evaporated. The crude product was chromatographed on silica gel eluting with 5% methanol in dichloromethane to give 0.24 g of oily material (47%), trans-1,3,4,4a,5,6,7,8,9,10a-Decahydro-6-[2,2-dimethyl-1-oxo-4-[(1-oxodecyl)oxy]butyl]-2-methylcyclopenta[4,5]pyrrolo[2,3-g]isoquinolin-10(2H)-one IR (CHCl₃), 1778 (C=O) and 1657 (C=O); NMR (CDCl₃), δ0.88 (t, 3, CH₃); 1.2–1.4 (m, 20, CH₂ and CH₃) 2.41 (5, 3, CH₃); 3.04 (br.d, 1, CH); 3.56 (br.d, 1, CH); 4.14 (t, 2, CH₂); MS m/e 512 (M+).

EXAMPLE 39 trans-6-[4-(4-Fluorophenyl)-4-oxobutyl]-1,4a,5,6,7,8-,8a,9-octahydro-2,3-dimethyl-1-[2,2-dimethyl-1-oxo-4-[(1-oxodecyl)oxy]-butyl]-4H-pyrrolo[2,3-g]isoquinolin-4-one To a solution of diisopropylamine (0.1 g) in tetrahydrofuran (5 mL) was added n-butyllithium in hexane (0.5 mL, 2M solution) at −30° C. and the solution was stirred at −20° to −30° C. for 15 minutes. To the solution was added at −40° C. (in one portion) trans-2,3-dimethyl-6-[4-(4-fluorophenyl)-4-oxobutyl]-1,4a,5,6,7,8-,8a,9-octahydro-4H-pyrrolo[2,3-g]-isoquinolin-4-one (0.19 g) and followed by 1 mL of hexamethylphosphoramide. The mixture was stirred at −10° to 0° C. for 30 minutes until a solution was formed. To the solution was added the crude 2,2-dimethyl-4-[(1-oxodecyl)oxy]-butanoyl chloride (0.305 g) in tetrahydrofuran (1 mL) at −30° C. and the mixture was stirred for 1 hour at −30° to −20° C. The solution was then poured onto ice water and was extracted in the dichloromethane. The combined extracts were washed with brine, dried (sodium sulfate) and evaporated. The crude product was chromatographed on silica gel eluting with 5% methanol in ethyl acetate to give 0.04 g of oily material (12.5%). trans-6-[4-(4-Fluorophenyl)-4-oxobutyl]-1,4a,5,6,7,8-

,8a,9-octahydro-2,3-dimethyl-1-[2,2-dimethyl-1-oxo-4-[(1-oxodecyl)oxy]-butyl]-4H-pyrrolo[2,3-g]isoquinolin-4-one NMR (CDCl$_3$) δ 0.87 (t, 3, CH$_3$); 1.21–1.32 (m, 20, CH$_2$ and CH$_3$); 1.31 (s, 6, CH$_3$); 2.1 and 2.19 (s, 6, CH$_3$); 3.63 (br.d, 1, CH); 7.13 and 8.0 (m, 4, phenyl); MS m/e 651 (M and H).

EXAMPLE 40

Formulation
Long-acting Depot Parenteral

| | |
|---|---|
| rac.-2,6-dimethyl-1-[2,2-dimethyl-4-[(1-oxodecyl)oxy]-1-oxobutyl]-3-ethyl-1,4a,5,6,7,-8,8a,9-octahydro-4a,8a-trans-4H—pyrrolo[2,3-g]isoquinolin-4-one | 250 mg |
| Sesame oil | 10 ml |

The ingredients are stirred in a flask for 15 hours at 20° C., and thereafter placed in an hermetically sealed vial and sterilized.

In a manner analogous to that described in Example 40, the following parenteral formulations can be prepared.

EXAMPLE 41

| | |
|---|---|
| rac.-2,6-dimethyl-1-[2,2-dimethyl-4-[(1-oxodecyl)oxy]-1-oxobutyl]-3-ethyl-1,4a,5,6,7,-8,8a,9-octahydro-4a,8a-trans-4H—pyrrolo[2,3-g]isoquinolin-4-one | 10 to 100 mg |
| α-tocopherol | 0.5 to 0.75 mg |
| Cottonseed Oil | q.s. to 1 ml |

EXAMPLE 42

| | |
|---|---|
| rac.-2,6-dimethyl-1-[2,2-dimethyl-4-[(1-oxodecyl)oxy]-1-oxobutyl]-3-ethyl-1,4a,5,6,7,-8,8a,9-octahydro-4a,8a-trans-4H-pyrrolo[2,3-g]isoquinolin-4-one | 10 to 100 mg |
| Ascorbyl Palmitate | 0.2 to 0.5 mg |
| Sesame Oil | q.s. to 1 ml |

EXAMPLE 43

| | |
|---|---|
| rac.-2,6-dimethyl-1-[2,2-dimethyl-4-[(1-oxodecyl)oxy]-1-oxobutyl]-3-ethyl-1,4a,5,6,7,-8,8a,9-octahydro-4a,8a-trans-4H—pyrrolo[2,3-g]isoquinolin-4-one | 10 to 100 |
| Propyl Gallate | 0.5 to 1 mg |
| Sesame Oil | q.s. to 1 ml |

EXAMPLE 44

| | |
|---|---|
| rac.-2,6-dimethyl-1-[2,2-dimethyl-4-[(1-oxodecyl)oxy]-1-oxobutyl]-3-ethyl-1,4a,5,6,7,-8,8a,9-octahydro-4a,8a-trans-4H—pyrrolo[2,3-g]isoquinolin-4-one | 10 to 100 mg |
| Monothioglycerol | 1 to 2 mg |
| Castor Oil | q.s. to 1 ml |

EXAMPLE 45

Multidose Formulation:
Long-Acting Depot Parenteral

| | |
|---|---|
| rac-2,6-dimethyl-1-[2,2-dimethyl-4-[(1-oxodecyl)oxy]-1-oxobutyl]-3-ethyl-1,4a,5,6,7,-8,8a,9-octahydro-4a,8a-trans-4H—pyrrolo[2,3-g]isoquinolin-4-one | 50 to 500 mg |
| α-tocopherol | 2.4 to 4.0 mg |
| Benzyl Alcohol | 50 to 100 mg |
| Sesame Oil | q.s. to 5 ml |

EXAMPLE 46

| | |
|---|---|
| rac.-2,6-dimethyl-1-[2,2-dimethyl-4-[(1-oxodecyl)oxy]-1-oxobutyl]-3-ethyl-1,4a,5,6,7,-8,8a,9-octahydro-4a,8a-trans-4H—pyrrolo[2,3-g]isoquionolin-4-one | 50 to 500 mg |
| α-tocopherol | 2.5 to 4.0 mg |
| Benzyl Alcohol | 5 to 10 mg |
| Sesame Oil | q.s. to 5 ml |

We claim:

1. A compound of the formula

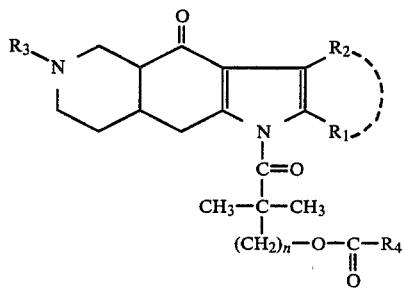

wherein R$_1$ and R$_2$ independently, are hydrogen, alkyl of 1 to 4 carbon atoms, cycloalkyl of 3 to 6 carbon atoms or alkenyl of 2 to 7 carbon atoms, or taken together are alkylene of 3 to 6 carbon atoms; and R$_3$ is hydrogen, alkyl of 1 to 24 carbon atoms, hydroxyalkyl of 1 to 24 carbon atoms, phenylhydroxyalkyl of 1 to 24 carbon atoms, halophenylhydroxyalkyl of 1 to 24 carbon atoms, alkylphenylhydroxyalkyl wherein alkyl is of 1 to 24 carbon atoms, alkoxyphenylhydroxyalkyl wherein alkoxy and alkyl each is of 1 to 24 carbon atoms, alkoxyalkyl wherein alkoxy and alkyl each is of 1 to 24 carbon atoms, aryloxyhydroxyalkyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkyl is 1 to 24 carbon atoms, alkoxyhydroxyalkyl wherein alkoxy and alkyl each is of 1 to 24 carbon atoms, alkanoyloxyalkyl wherein alkanoyl is of 1 to 7 carbon atoms and alkyl is of 1 to 24 carbon atoms, benzoyloxyalkyl wherein alkyl is of 1 to 24 carbon atoms, arylcarbonylalkyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkyl is 1 to 24 carbon atoms, alkoxycarbonylalkyl wherein alkoxy and alkyl each is of 1 to 24 carbon atoms, aralkyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkyl is 1 to 24 carbon atoms, alkenyl of 2 to 7 carbon atoms, alkylcycloalkyl wherein cyclo-alkyl is of 3 to 6 carbon atoms and alkyl is of 1 to 24 carbon atoms, alkynyl of 2 to 7 carbon atoms, thienylalkyl of 1 to 24 carbon atoms, furylalkyl of 1 to 24 carbon atoms, arylcarboxamidoalkyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkyl is 1 to 24 carbon atoms, alkanoylalkyl wherein alkanoyl is of 1 to 7 carbon atoms and alkyl is of 1 to 24 carbon atoms, benzoylalkyl wherein alkyl is of 1 to 24 carbon atoms, cyclic-alkyloxoalkyl wherein cyclic-alkyl is of 3 to 6 carbon atoms and alkyl is of 1 to 24 carbon atoms, cyclic-alkylhydroxyalkyl wherein cyclic-alkyl is of 3 to 6 carbon atoms and alkyl is of 1 to 24 carbon atoms, alkenyloxyalkyl wherein alkenyl is of 2 to 7 carbon atoms and alkyl is of 1 to 24 carbon atoms, aralkenyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkenyl is 2 to 7 carbon atoms, aryloxyalkyl wherein aryl is phenyl or phenyl bearing one or more substituents selected from the group consisting of halogen, trifluoromethyl, alkyl of 1 to 24 carbon atoms, alkoxy of 1 to 24 carbon atoms nitro, amino, alkyl of 1 to 24 carbon atoms-amino, and di-alkyl of 1 to 24 carbon atoms-amino, and alkyl is 1 to 24 carbon atoms, or aryl-N-imidazolonylalkyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkyl is 1 to 24 carbon atoms; $R_4$ is alkyl of 1 to 24 carbon atoms, and n is the integer 2 or 3, a corresponding optical isomer, a corresponding geometric isomer or a mixture thereof, or a pharmaceutically acceptable acid addition salt thereof.

2. A compound, in accordance with claim 1, of the formula

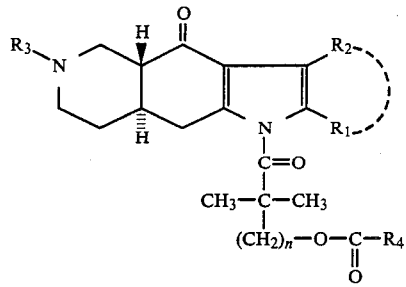

trans-I wherein $R_1$ and $R_2$ independently, are hydrogen, alkyl of 1 to 4 carbon atoms, cycloalkyl of 3 to 6 carbon atoms or alkenyl of 2 to 7 carbon atoms, or taken together are alkylene of 3 to 6 carbon atoms; and $R_3$ is hydrogen, alkyl of 1 to 24 carbon atoms, hydroxyalkyl of 1 to 24 carbon atom, phenylhydroxyalkyl of 1 to 24 carbon atoms, halophenylhydroxyalkyl of 1 to 24 carbon atoms, alkylphenylhydroxyalkyl wherein alkyl is of 1 to 24 carbon atoms, alkoxyphenylhydroxyalkyl wherein alkoxy and alkyl each is of 1 to 24 carbon atoms, alkoxyalkyl wherein alkoxy and alkyl each is of 1 to 24 carbon atoms, aryloxyhydroxyalkyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkyl is 1 to 24 carbon atoms, alkoxyhydroxyalkyl wherein alkoxy and alkyl each is of 1 to 24 carbon atoms, alkanoyloxyalkyl wherein alkanoyl is of 1 to 7 carbon atoms and alkyl is of 1 to 24 carbon atoms, benzoyloxyalkyl wherein alkyl is of 1 to 24 carbon atoms, arylcarbonylalkyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkyl is 1 to 24 carbon atoms, alkoxycarbonylalkyl wherein alkoxy and alkyl each is of 1 to 24 carbon atoms, aralkyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkyl is 1 to 24 carbon atoms, alkenyl of 2 to 7 carbon atoms, alkylcycloalkyl wherein cyclo-alkyl is of 3 to 6 carbon atoms and alkyl is of 1 to 24 carbon atoms, alkynyl of 2 to 7 carbon atoms, thienylalkyl of 1 to 24 carbon atoms, furylalkyl of 1 to 24 carbon atoms, arylcarboxamidoalkyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkyl is 1 to 24 carbon atoms, alkanoylalkyl wherein alkanoyl is of 1 to 7 carbon atoms and alkyl is of 1 to 24 carbon atoms, benzoylalkyl wherein alkyl is of 1 to 24 carbon atoms, cyclic-alkyloxoalkyl wherein cyclic-alkyl is of 3 to 6 carbon atoms and alkyl is of 1 to 24 carbon atoms, cyclic-alkylhydroxyalkyl wherein cyclic-alkyl is of 3 to 6 carbon atoms and alkyl is of 1 to 24 carbon atoms, alkenyloxyalkyl wherein alkenyl is of 2 to 7 carbon atoms and alkyl is of 1 to 24 carbon atoms, aralkenyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkenyl is of 2 to 7 carbon atoms, aryloxyalkyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkyl is 1 to 24 carbon atoms, or aryl-N-imidazolonylalkyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkyl is 1 to 24 carbon atoms; $R_4$ is alkyl of 1 to 24 carbon atoms, and n is the integer 2 or 3, a corresponding optical isomer, a corresponding geometric isomer or a mixture thereof, or a pharmaceutically acceptable acid addition salt thereof.

3. A compound, in accordance with claim 2, wherein $R_1$ and $R_2$ are alkyl of 1 to 4 carbon atoms or taken together are alkylene of 3 to 4 carbon atoms, $R_3$ is alkyl, arylcarbonylalkyl or aralkyl and n is 2.

4. A compound, in accordance with claim 3, wherein $R_1$ and $R_2$ are alkyl of 1 to 4 carbon atoms, $R_3$ is alkyl, and $R_4$ is alkyl of 7 to 11 carbon atoms.

5. A compound, in accordance with claim 4, of the formula trans-I which is the 4aR,8aR-enantiomer.

6. A compound, in accordance with claim 1, racemic 2,6-dimethyl-1-[2,2-dimethyl-4-[(1-oxodecyl)oxy]-2,6-1-oxobutyl]-3-ethyl-1,4a,5,6,7,8,8a,9-octahydro-4a,8a-trans-4H-pyrrolo[2,3-g]isoquinolin-4-one.

7. A compound, in accordance with claim 6, which is trans-(-)-2,6-dimethyl-1-[2,2-dimethyl-4-[(1-oxodecyl)oxy]-1-oxobutyl]-3-ethyl-1,4a,5,6,7,8,8a,9-octahydro-4aR,8aR-4H-pyrrolo[2,3-g]isoquinolin-4-one.

8. A compound, in accordance with claim 1, which is trans-6-[4-(4-fluorophenyl)-4-oxobutyl]-1,4a,5,6,7,8-,8a,9-octahydro-2,3-dimethyl-1-[2,2-dimethyl-1-oxo-4-[(1-oxodecyl)oxy]-butyl]-4H-pyrrolo[2,3-g]isoquinolin-4-one.

9. A compound of the formula

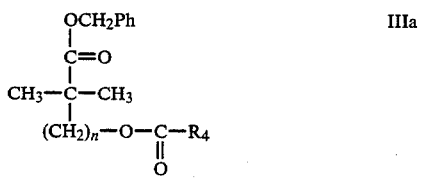

IIIa wherein $R_4$ is alkyl of 1 to 24 carbon atoms, Ph is phenyl, and n is the integer 2 or 3.

10. A compound, in accordance with claim 9, wherein n is 2, and $R_4$ is alkyl of 7 to 11 carbon atoms.

11. A compound, in accordance with claim 9, which is 2,2-dimethyl-4[(1-oxodecyl)oxy]butanoic acid phenylmethyl ester.

12. A compound of the formula

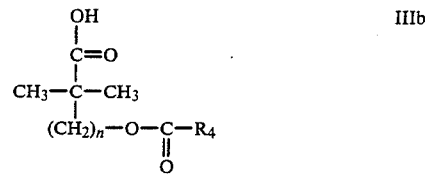

IIIb wherein $R_4$ is alkyl of 1 to 24 carbon atoms and n is the integer 2 or 3.

13. A compound, in accordance with claim 12, wherein n is 2, and $R_4$ is alkyl of 7 to 11 carbon atoms.

14. A compound, in accordance with claim 12, which is 2,2-dimethyl-4-[(1-oxodecyl)oxy]butanoic acid.

15. A compound of the formula

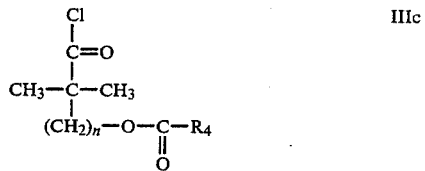

IIIc wherein $R_4$ is alkyl of 1 to 24 carbon atoms, Cl is chlorine and n is the integer 2 or 3.

16. A compound, in accordance with claim 15, wherein n is 2, and $R_4$ is alkyl of 7 to 11 carbon atoms.

17. A compound, in accordance with claim 15, which is 2,2-dimethyl-4-[(1-oxodecyl)oxy]butanoyl chloride.

18. An antipsychotic pharmaceutical composition comprising an antipsychotically effective amount of a compound of the formula

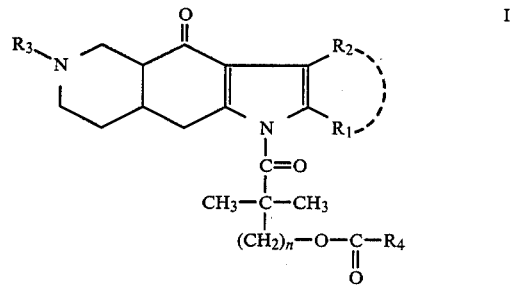

I wherein $R_1$ and $R_2$ independently, are hydrogen, alkyl of 1 to 4 carbon atoms, cycloalkyl of 3 to 6 carbon atoms or alkenyl of 2 to 7 carbon atoms, or taken together are alkylene of 3 to 6 carbon atoms; and $R_3$ is hydrogen, alkyl of 1 to 24 carbon atoms, hydroxyalkyl of 1 to 24 carbon atoms, phenylhydroxyalkyl of 1 to 24 carbon atoms, halophenylhydroxyalkyl of 1 to 24 carbon atoms, alkylphenylhydroxyalkyl wherein alkyl is of 1 to 24 carbon atoms, alkoxyphenylhydroxyalkyl wherein alkoxy and alkyl each is of 1 to 24 carbon atoms, alkoxyalkyl wherein alkoxy and alkyl each is of 1 to 24 carbon atoms, aryloxyhydroxyalkyl wherein aryl is phenyl or phenyl bearing one or more substituents selected from the group consisting of halogen, trifluoromethyl, lower alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkyl is 1 to 24 carbon atoms, alkoxyhydroxyalkyl wherein alkoxy and alkyl each is of 1 to 24 carbon atoms, alkanoyloxyalkyl wherein alkanoyl is of 1 to 7 carbon atoms and alkyl is of 1 to 24 carbon atoms, benzoyloxyalkyl wherein alkyl is of 1 to 24 carbon atoms, arylcarbonylalkyl wherein aryl is phenyl or phenyl bearing one or more substituents selected from the group consisting of halogen, trifluoromethyl, lower alkyl of 1 to 24 carbon atoms, alkoxy of 1 to 24 carbon atoms, nitro, amino, lower alkyl of 1 to 24 carbon atoms-amino and di-alkyl of 1 to 24 carbon atoms-amino, and alkyl is 1 to 24 carbon atoms, alkoxycarbonylalkyl wherein alkoxy and alkyl each is of 1 to 24 carbon atoms, aralkyl wherein aryl is phenyl or phenyl bearing one or more substituents selected from the group consisting of halogen, trifluoromethyl, lower alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkyl is 1 to 24 carbon atoms, alkenyl of 2 to 7 carbon atoms, alkylcycloalkyl wherein cyclo-alkyl is of 3 to 6 carbon atoms and alkyl is of 1 to 24 carbon atoms, alkynyl of 2 to 7 carbon atoms, thienylalkyl of 1 to 24 carbon atoms, furylalkyl of 1 to 24 carbon atoms, arylcarboxamidoalkyl wherein aryl is phenyl or phenyl bearing one or more substituents selected from the group consisting of halogen, trifluoromethyl, lower alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkyl is 1 to 24 carbon atoms, alkanoylalkyl wherein alkanoyl is of 1 to 7 carbon atoms and alkyl is of 1 to 24 carbon atoms, benzoylalkyl wherein alkyl is of 1 to 24 carbon atoms, cyclic-alkyloxoalkyl wherein cyclic-alkyl is of 3 to 6 carbon atoms and alkyl is of 1 to 24 carbon atoms, cyclic-alkylhydroxyalkyl wherein cyclic-alkyl is of 3 to 6 carbon atoms and alkyl is of 1 to 24 carbon atoms, alkenyloxyalkyl wherein alkenyl is of 2 to 7 carbon atoms and alkyl is of 1 to 24 carbon atoms, aralkenyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkenyl is of 2 to 7 carbon atoms, aryloxyalkyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino and alkyl is 1 to 24 carbon atoms, or aryl-N-imidazolonylalkyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkyl is 1 to 24 carbon atoms; $R_4$ is alkyl of 1 to 24 carbon atoms, and n is the integer 2 or 3, a corresponding optical isomer, a corresponding geometric isomer or a mixture thereof, or a pharmaceutically acceptable acid addition salt thereof.

19. An antipsychotic pharmaceutical composition, in accordance with claim 18, wherein the compound of formula I is a compound of the formula

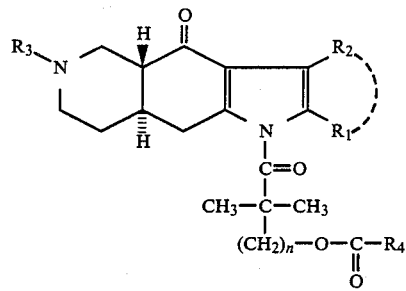

trans-I wherein $R_1$ and $R_2$ independently, are hydrogen, alkyl of 1 to 4 carbon atoms, cycloalkyl of 3 to 6 carbon atoms or alkenyl of 2 to 7 carbon atoms, or taken together are alkylene of 3 to 6 carbon atoms; and $R_3$ is hydrogen, alkyl of 1 to 24 carbon atoms, hydroxyalkyl of 1 to 24 carbon atoms, phenylhydroxyalkyl of 1 to 24 carbon atoms, halophenylhydroxyalkyl of 1 to 24 carbon atoms, alkylphenylhydroxyalkyl wherein alkyl is of 1 to 24 carbon atoms, alkoxyphenylhydroxyalkyl wherein alkoxy and alkyl each is of 1 to 24 carbon atoms, alkoxyalkyl wherein alkoxy and alkyl each is of 1 to 24 carbon atoms, aryloxyhydroxyalkyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkyl is 1 to 24 carbon atoms, alkoxyhydroxyalkyl wherein alkoxy and alkyl each is of 1 to 24 carbon atoms, alkanoyloxyalkyl wherein alkanoyl is of 1 to 7 carbon atoms and alkyl is of 1 to 24 carbon atoms, benzoyloxyalkyl wherein alkyl is of 1 to 24 carbon atoms, arylcarbonylalkyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkyl is 1 to 24 carbon atoms, alkoxycarbonylalkyl wherein alkoxy and alkyl each is of 1 to 24 carbon atoms, aralkyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkyl is 1 to 24 carbon atoms, alkenyl of 2 to 7 carbon atoms, alkylcycloalkyl wherein cyclo-alkyl is of 3 to 6 carbon atoms and alkyl is of 1 to 24 carbon atoms, alkynyl of 2 to 7 carbon atoms, thienylalkyl of 1 to 24 carbon atoms, furylalkyl of 1 to 24 carbon atoms, arylcarboxamidoalkyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkyl is 1 to 24 carbon atoms, alkanoylalkyl wherein alkanoyl is of 1 to 7 carbon atoms and alkyl is of 1 to 24 carbon atoms, benzoylalkyl wherein alkyl is of 1 to 24 carbon atoms, cyclic-alkyloxoalkyl wherein cyclic-alkyl is of 3 to 6 carbon atoms and alkyl is of 1 to 24 carbon atoms, cyclic-alkylhydroxyalkyl wherein cyclic-alkyl is of 3 to 6 carbon atoms and alkyl is of 1 to 24 carbon atoms, alkenyloxyalkyl wherein alkenyl is of 2 to 7 carbon atoms and alkyl is of 1 to 24 carbon atoms, aralkenyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkenyl is of 2 to 7 carbon atoms, aryloxyalkyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino and alkyl is 1 to 24 carbon atoms, or aryl-N-imidazolonylalkyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkyl is 1 to 24 carbon atoms; $R_4$ is alkyl of 1 to 24 carbon atoms, and n is the integer 2 or 3, a corresponding optical isomer, a corresponding geometric isomer or a mixture thereof, or a pharmaceutically acceptable acid addition salt thereof.

20. A method of treating psychoses which comprises administering to a host requiring such treatment an antipsychotically effective amount of a compound of the formula

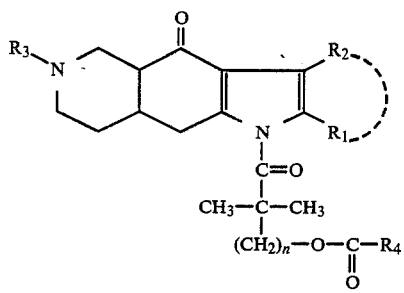

wherein $R_1$ and $R_2$ independently, are hydrogen, alkyl of 1 to 4 carbon atoms, cycloalkyl of 3 to 6 carbon atoms or alkenyl of 2 to 7 carbon atoms, or taken together are alkylene of 3 to 6 carbon atoms; and $R_3$ is hydrogen, alkyl of 1 to 24 carbon atoms, hydroxyalkyl of 1 to 24 carbon atoms, phenylhydroxyalkyl of 1 to 24 carbon atoms, halophenylhydroxyalkyl of 1 to 24 carbon atoms, alkylphenylhyroxyalkyl wherein alkyl is of 1 to 24 carbon atoms, alkoxyphenylhydroxyalkyl wherein alkoxy and alkyl each is of 1 to 24 carbon atoms, alkoxyalkyl wherein alkoxy and alkyl each is of 1 to 24 carbon atoms, aryloxyhydroxyalkyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkyl is 1 to 24 carbon atoms, alkoxyhydroxyalkyl wherein alkoxy and alkyl each is of 1 to 24 carbon atoms, alkanoyloxyalkyl wherein alkanoyl is of 1 to 7 carbon atoms and alkyl is of 1 to 24 carbon atoms, benzoyloxyalkyl wherein alkyl is of 1 to 24 carbon atoms, arylcarbonylalkyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkyl is 1 to 24 carbon atoms, alkoxycarbonylalkyl wherein alkoxy and alkyl each is of 1 to 24 carbon atoms, aralkyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkyl is 1 to 24 carbon atoms, alkenyl of 2 to 7 carbon atoms, alkylcycloalkyl wherein cyclo-alkyl is of 3 to 6 carbon atoms and alkyl is of 1 to 24 carbon atoms, alkynyl of 2 to 7 carbon atoms, thienylalkyl of 1 to 24 carbon atoms, furylalkyl of 1 to 24 carbon atoms, arylcarboxamidoalkyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkyl is 1 to 24 carbon atoms, alkanoylalkyl wherein alkanoyl is of 1 to 7 carbon atoms and alkyl is of 1 to 24 carbon atoms, benzoylalkyl wherein alkyl is of 1 to 24 carbon atoms, cyclic-alkyloxoalkyl wherein cyclic-alkyl is of 3 to 6 carbon atoms and alkyl is of 1 to 24 carbon atoms, cyclic-alkylhydroxyalkyl wherein cyclic-alkyl is of 3 to 6 carbon atoms and alkyl is of 1 to 24 carbon atoms, alkenyloxyalkyl wherein alkenyl is of 2 to 7 carbon atoms and alkyl is of 1 to 24 carbon atoms, aralkenyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkenyl is of 2 to 7 carbon atoms, aryloxyalkyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino and alkyl is 1 to 24 carbon atoms, or aryl-N-imidazolonylalkyl wherein aryl is phenyl or phenyl bearing one or more substituents selected from the group consisting of halogen, trifluoromethyl alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkyl is 1 to 24 carbon atoms; R₄ is alkyl of 1 to 24 carbon atoms, and n is the integer 2 or 3, a corresponding optical isomer, a corresponding geometric isomer or a mixture thereof, or a pharmaceutically acceptable acid addition salt thereof.

21. A method, in accordance with claim 20, wherein the compound utilized is a compound of the formula

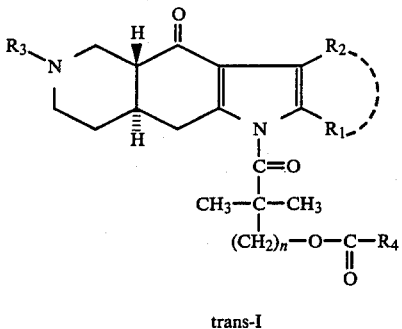

trans-I wherein $R_1$ and $R_2$ independently, are hydrogen, alkyl of 1 to 4 carbon atoms, cycloalkyl of 3 to 6 carbon atoms or alkenyl of 2 to 7 carbon atoms, or taken together are alkylene of 3 to 6 carbon atoms; and $R_3$ is hydrogen, alkyl of 1 to 24 carbon atoms, hydroxyalkyl of 1 to 24 carbon atoms, phenylhydroxyalkyl of 1 to 24 carbon atoms, halophenylhydroxyalkyl of 1 to 24 carbon atoms, alkylphenylhydroxyalkyl wherein alkyl is of 1 to 24 carbon atoms, alkoxyphenylhydroxyalkyl wherein alkoxy and alkyl each is of 1 to 24 carbon atoms, alkoxyalkyl wherein alkoxy and alkyl each is of 1 to 24 carbon atoms, aryloxyhydroxyalkyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl is of to 24 carbon atoms-amino, and alkyl is 1 to 24 carbon atoms, alkoxyhydroxyalkyl wherein alkoxy and alkyl each is of 1 to 24 carbon atoms, alkanoyloxyalkyl wherein alkanoyl is of 1 to 7 carbon atoms and alkyl is of 1 to 24 carbon atoms, benzoyloxyalkyl wherein alkyl is of 1 to 24 carbon atoms, arylcarbonylalkyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkyl is 1 to 24 carbon atoms, alkoxycarbonylalkyl wherein alkoxy and alkyl each is of 1 to 24 carbon atoms, aralkyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkyl is 1 to 24 carbon atoms, alkenyl of 2 to 7 carbon atoms, alkylcycloalkyl wherein cyclo-alkyl is of 3 to 6 carbon atoms and alkyl is of 1 to 24 carbon atoms, alkynyl of 2 to 7 carbon atoms, thienylalkyl of 1 to 24 carbon atoms, furylalkyl of 1 to 24 carbon atoms, arylcarboxamidoalkyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkyl is 1 to 24 carbon atoms, alkanoylalkyl wherein alkanoyl is of 1 to 7 carbon atoms and alkyl is of 1 to 24 carbon atoms, benzoylalkyl wherein alkyl is of 1 to 24 carbon atoms, cyclicalkyloxoalkyl wherein cyclic-alkyl is of 3 to 6 carbon atoms and alkyl is of 1 to 24 carbon atoms, cyclic-alkylhydroxyalkyl wherein cyclic-alkyl is of 3 to 6 carbon atoms and alkyl is of 1 to 24 carbon atoms, alkenyloxyalkyl wherein alkenyl is of 2 to 7 carbon atoms and alkyl is of 1 to 24 carbon atoms, aralkenyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkenyl is of 2 to 7 carbon atoms, aryloxyalkyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-alkyl of 1 to 24 carbon atoms-amino, and alkyl is 1 to 24 carbon atoms, or aryl-N-imidazoloxylalkyl wherein aryl is phenyl or phenyl bearing one or more substituents selected from the group consisting of halogen, trifluoromethyl, alkyl of 1 to 24 carbon atoms, alkoxy of 1 to 24 carbon atoms, nitro, amino, alkyl of 1 to 24 carbon atoms-amino and di-lower alkyl of 1 to 24 carbon atoms-amino, and alkyl is 1 to 24 carbon atoms; $R_4$ is alkyl of 1 to 24 carbon atoms, and n is the integer 2 or 3, a corresponding optical isomer, a corresponding geometric isomer or a mixture thereof, or a pharmaceutically acceptable acid addition salt thereof.

22. A method, in accordance with claim 21, wherein $R_1$ and $R_2$ are alkyl of 1 to 4 carbon atoms or taken together are alkylene of 3 to 4 carbon atoms, $R_3$ is alkyl, arylcarbonylalkyl or aralkyl and n is 2.

23. A method, in accordance with claim 22, wherein $R_1$ and $R_2$ are alkyl of 1 to 4 carbon atoms and $R_3$ is alkyl.

24. A method, in accordance with claim 23, wherein the compound of formula I is a compound of the formula trans-I which is the 4aR,8aR enantiomer.

25. A method in accordance with claim 20, wherein the compound of formula I is racemic 2,6-dimethyl-1-[2,2-dimethyl-4-[(1-oxodecyl)oxy]-1-oxobutyl]-3-ethyl-1,4a,5,6,7,8,8a,9-octahydro-4a,8a-trans-4H-pyrrolo[2,3-g]isoquinolin-4-one.

26. A method, in accordance with claim 25, wherein the compound of formula I is trans-(−)-2,6-dimethyl-1-[2,2-dimethyl-4-[(1-oxodecyl)oxy]-1-oxobutyl]-3-ethyl-1,4a,5,6,7,8,8a, 9-octahydro-4aR,8aR-4H-pyrrolo[2,3-g]isoquinolin-4-one.

27. A method, in accordance with claim 20, wherein the compound of formula I is trans-6-[4-(4-fluorophenyl)-4-oxobutyl]-1,4a,5,6,7,8,8a,9-octahydro-2,3-dimethyl-1-[2,2-dimethyl-1-oxo-4-[(1-oxodecyl)oxy]-butyl]-4H-pyrrolo[2,3-g]isoquinolin-4-one.

28. A pharmaceutical composition, in accordance with claim 19, wherein $R_1$ and $R_2$ are alkyl of 1 to 4 carbon atoms or taken together are alkylene of 3 to 4 carbon atoms, $R_3$ is alkyl, arylcarbonylalkyl or aralkyl and n is 2.

29. A pharmaceutical composition, in accordance with claim 28, wherein $R_1$ and $R_2$ are alkyl or 1 to 4 carbon atoms and $R_3$ is alkyl.

30. A pharmaceutical composition, in accordance with claim 29, wherein the compound of formula I is a compound of the formula trans-I which is the 4aR,8aR enantiomer.

31. A pharmaceutical composition, in accordance with claim 18, wherein the compound of formula trans-I is racemic 2,6-dimethyl-1-[2,2-dimethyl-4-[(1-oxodecyl)oxy]-1-oxobutyl]-3-ethyl-1,4a,5,6,7,8,8a,9-octahydro-4a,8a-trans-4H-pyrrolo[2,3-g]isoquinolin-4-one.

32. A pharmaceutical composition, in accordance with claim 31, which is trans-(−)-2,6-dimethyl-1-[2,2-dimethyl-4-[(1-oxodecyl)-oxy]-1-oxobutyl]-3-ethyl-1,4a,5,6,7,8,8a,9-octahydro-4aR,8aR-4H-pyrrolo[2,3-g]isoquinolin-4-one.

33. A pharmaceutical composition in accordance with claim 18, which is trans-6-[4-(4-fluorophenyl)-4-oxobutyl]-1,4a,5,6,7,8,8a,9-octahydro-2,3-dimethyl-1-[2,2-dimethyl-1-oxo-4-[(1-oxodecyl)oxy]-butyl]-4H-pyrrolo[2,3-g]isoquinolin-4-one.

* * * * *